United States Patent
Roervig et al.

(10) Patent No.: US 10,137,252 B2
(45) Date of Patent: Nov. 27, 2018

(54) PEN-SHAPED TORSION SPRING DRIVEN INJECTION DEVICE

(71) Applicant: Novo Nordisk A/S, Bagsvaerd (DK)

(72) Inventors: Simon Roervig, Copenhagen OE (DK); Christian Peter Enggaard, Vejby (DK); Nikolaj Eusebius Jakobsen, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 209 days.

(21) Appl. No.: 15/317,463

(22) PCT Filed: Jun. 23, 2015

(86) PCT No.: PCT/EP2015/064131
§ 371 (c)(1),
(2) Date: Dec. 9, 2016

(87) PCT Pub. No.: WO2015/197629
PCT Pub. Date: Dec. 30, 2015

(65) Prior Publication Data
US 2017/0119973 A1    May 4, 2017

(30) Foreign Application Priority Data
Jun. 26, 2014 (EP) .................. 14174108

(51) Int. Cl.
*A61M 3/00* (2006.01)
*A61M 5/315* (2006.01)
(Continued)

(52) U.S. Cl.
CPC .......... *A61M 5/31553* (2013.01); *A61M 5/20* (2013.01); *A61M 5/2033* (2013.01);
(Continued)

(58) Field of Classification Search
CPC .... A61M 2005/202; A61M 2005/2444; A61M 2005/3126; A61M 2205/585; A61M 5/20;
(Continued)

(56) References Cited

U.S. PATENT DOCUMENTS

| 5,104,380 A | 4/1992 | Holman et al. |
| 2006/0054326 A1 | 3/2006 | Alves et al. |

(Continued)

FOREIGN PATENT DOCUMENTS

| WO | 02/053214 A1 | 7/2002 |
| WO | 2006/003130 A1 | 1/2006 |
| WO | 2013/178372 A1 | 12/2013 |

*Primary Examiner* — Jason Flick
(74) *Attorney, Agent, or Firm* — Wesley Nicolas

(57) ABSTRACT

The invention relates to a pen-shaped torsion spring driven injection device for apportioning set dose of a liquid drug. A piston rod having an external thread is driven forward by a rotatable piston rod guide engaging the piston rod. The piston rod guide is rotated by a torsion spring encompassed between the housing and the piston rod guide. A scale drum having a thread engaging the external thread of the piston rod is provided, and the scale drum is rotated up and down the piston rod by a proximal located rotatable dose setting member cooperating with the scale drum. The scale drum thus move helically when rotated as the piston rod is held inrotatable during dose setting.

15 Claims, 11 Drawing Sheets

(51) Int. Cl.
*A61M 5/20* (2006.01)
*A61M 5/24* (2006.01)
*A61M 5/31* (2006.01)

(52) U.S. Cl.
CPC .......... *A61M 5/24* (2013.01); *A61M 5/31583* (2013.01); *A61M 2005/202* (2013.01); *A61M 2005/2444* (2013.01); *A61M 2005/3126* (2013.01); *A61M 2205/585* (2013.01)

(58) Field of Classification Search
CPC .. A61M 5/2033; A61M 5/24; A61M 5/31553; A61M 5/31583
USPC .......................................................... 604/189
See application file for complete search history.

(56) References Cited

U.S. PATENT DOCUMENTS

| | | | |
|---|---|---|---|
| 2009/0293870 A1 | 12/2009 | Brunnberg et al. | |
| 2010/0114025 A1* | 5/2010 | Moller .................... | A61M 5/20 604/135 |
| 2011/0054412 A1* | 3/2011 | Eich ........................ | A61M 5/20 604/207 |
| 2012/0029443 A1* | 2/2012 | Holmqvist .............. | A61M 5/20 604/211 |
| 2012/0046613 A1 | 2/2012 | Plumptre | |

* cited by examiner

"First Position"

"Second position"

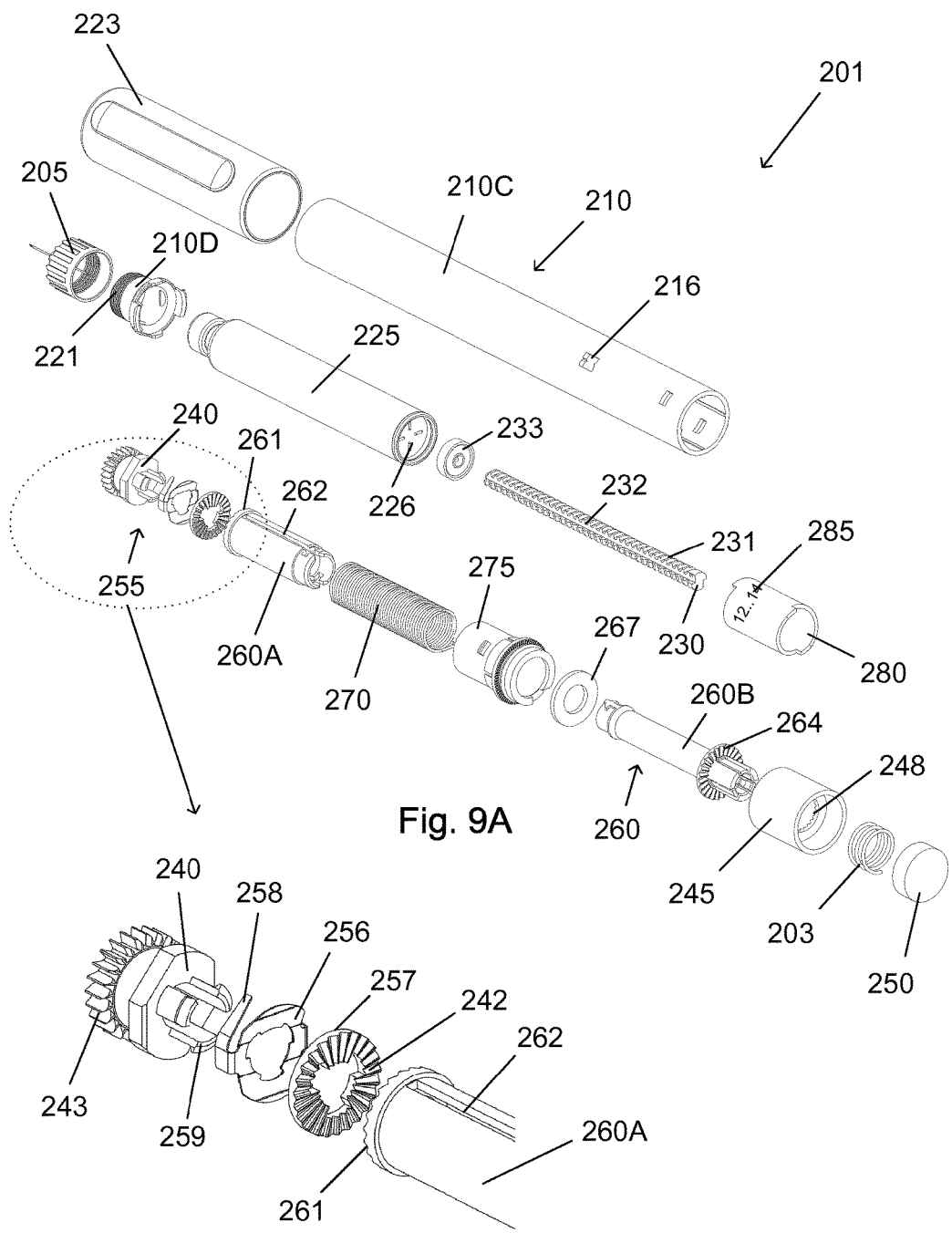

PEN-SHAPED TORSION SPRING DRIVEN INJECTION DEVICE

CROSS-REFERENCE TO RELATED APPLICATIONS

This application is a 35 U.S.C. § 371 National Stage application of International Application PCT/EP2015/064131 (published as WO 2015/197629), filed Jun. 23, 2015, which claims priority to European Patent Application 14174108.2, filed Jun. 26, 2014; the contents of which are incorporated herein by reference.

THE TECHNICAL FIELD OF THE INVENTION

The invention relates to a pen-shaped injection device, such as a purely mechanical pen-shaped injection device in which the expelling of the individually set doses is driven by a torsion spring.

DESCRIPTION OF RELATED ART

Spring operated injection devices wherein the injection is driven by a torsion spring has been known for decades. An example of such early torsion spring injection device is provided in U.S. Pat. No. 5,104,380. However, this automatic injection device has no separate scale drum and the set dose is visualized only by the rotational position of the dose setting button in relation to the housing. This strongly reduces the number of possible settings since a user, even with impaired sight, must be able to visually see the indicia indicating the dose sizes.

For more modern injection devices it is almost a requirement that the injection device can display a high number of different dose settings. It has therefore become state-of-art to implement a helical movable scale drum in the injection device. Due to the helical movement of the scale drum it has been possible to display a high number of different dose sizes. However, the presence of such helical movable scale drum makes the injection device rather thick and bulky.

Examples of spring operated injection devices having a helical movable scale drum for indicating the set doses are provided in US 2011/0054412 and in WO 2002/053214.

US 2011/0054412 disclose a spring driven injection device in which the torsion spring is a so-called clock spring encompassed between the housing and a drive shaft. The clock spring is torsional strained when a dose is set and released during dosing to drive the drive shaft which via a dose mechanism moves a piston rod forward inside the cartridge.

It can be seen from this reference that a clock spring is meant to be a wounded spring where all the windings are provided consecutively upon each other without any helical extension. Such clock springs are usually wounded from a steel tape and the width of such clock spring is therefore the same as the width of the steel tape from which the spring is wounded. Common for clock spring is further that they operate as torsion springs thus applying a rotational torque. Clock springs are also often referred to as constant force spring since they tend to deliver a constant force when they recoil.

The injection device disclosed in US 2011/0054412 is a tubular pen-shaped device which seems to be the shape preferred by many users. Such injection device usually comprises several constructional layers which often makes such pen shaped injection devices rather thick and bulky. As disclosed the outer layer (not considering the housing itself) is a scale drum which is helically guided in a thread provided on the inner surface of the housing.

In the injection device disclosed in WO 2002/053214, the scale drum is driven directly on the piston rod which makes it possible to avoid threads on the inside surface of the housing. However, the spring used is a helical wounded compression spring providing an axial force which requires additional constructional elements inside the injection device to transform this axial force to a rotation of the piston rod, and such additional elements adds to the overall diameter of the injection device.

DESCRIPTION OF THE INVENTION

It is an object of the present invention to provide a pen-shaped injection having the ability to display a high number of different dose sizes and in which the numbers of constructional layers have been reduced thereby reducing the outside diameter of the injection device.

The invention is defined in the attached claim 1 followed by a number of embodiments. The individual claims are explained in details in the following.

Accordingly, in one aspect of the present invention a pen-shaped torsion spring driven injection device for apportioning set doses of a liquid drug is provided. The torsion spring driven injection device comprises the following main components:

A housing which is provided with a window,
A piston rod having an external thread and preferably a non-circular cross section,
A rotatable piston rod guide which engages and drives the piston rod at least during dose expelling,
A torsion spring for rotating the piston rod guide at least during dose expelling,
A rotatable scale drum with a thread engaging the external thread of the piston rod and which scale drum carries a plurality of indicia wherein at least a subset of the plurality of indicia is viewable through the window,
A proximally located rotatable dose setting member which cooperates with the scale drum such that rotation of the dose setting member at least during dose setting is transformed to a rotation of the scale drum.

Further, when setting a dose, the piston rod is held inrotatable whereby the scale drum rotates helically on the external thread of the piston rod.

The operable connection between the dose setting member and the scale drum can be geared such that the rotational modus is different for the dose setting button and for the scale drum. The scale drum thus travels axially and rotates on the piston rod at the same time whenever the dose setting button is rotated. During this helical movement, the scale drum passes by the window in the housing such that the user visibly can inspect the indicia provided on the scale drum as the dose is being set. The window can be covered by a transparent material which in one example is shaped as a magnifier, alternatively the window can be any kind of opening in the housing through which a user can visibly inspect the indicia.

During dose setting, the scale drum rotates helically whereas the piston rod is held inrotatable. This can in one example be done by securing the piston rod guide rotational to the housing at least in one rotational direction and to have the piston rod guide engage with the non-circular cross-section of the piston rod. The prevented rotational direction being one that would move the piston rod proximally, thus the mechanism only allows the piston rod to move distally.

The indicia are also successively viewable during expelling of the dose as the scale drum rotates back to its initial position. During expelling of the dose the rotation of the scale drum back to its initial position is accompanied by a movement of the piston rod in the distal direction thus moving the piston rod further into the cartridge to thereby expel the set dose.

In a further example, the torsion spring for driving out the set dose is operable between a driver element and a part of the housing. A part of the housing can be either a part stationary coupled to the housing or it can be an integral part of the housing.

The driver element is coupled to the dose setting button at least during dose setting meaning that the driver element can be de-coupled from the dose setting button when the set dose is injected. This has the effect that when the driver element rotates during dose expelling, the dose setting button is de-coupled and thus do not rotate.

Further, the torsion spring which at one end is connected to the driver element to rotate this has the opposite end connected to the housing, or at least to a part of the housing. The torsion spring thus delivers a torque between the housing of the injection device and the driver element.

In one example, the part connected to the housing could be a proximal located separate part which closes the housing and e.g. functions as a base for the torsion spring. This separate part could be connected to the housing by welding, by gluing or simply by being click-fitted or press-fitted to the housing. However many other assembly methods can be utilized.

In a further aspect the scale drum has at least a part which extends through the driver element to engage the piston rod. The scale drum has an outer surface which carries the indicia and which outer surface is visible through the window in the housing as it rotates pass the window. At the centre of the scale drum a thread traveling on the thread of the piston rod is provided. This thread can be connected to the outer surface in multiple ways.

In one example, the thread surrounding the piston rod is created in an element which is connected to the outer surface through one or more arms. Both the element carrying the thread, the arms and the outer surface can be manufactured as separate elements which are then connected to form an assembly. They parts can alternatively be made as one unison scale drum element e.g. through injection moulding.

In a further example, the driver element is provided with a longitudinal opening through which at least the part of the scale drum extends to engage the piston rod. The longitudinal opening allows for relative axial motion between the driver element and the scale drum.

The part extending through the longitudinal opening of the scale drum is preferably a number of radial arms connecting the outer surface and the element carrying the thread. Rotation of the driver element is thus conveyed to the scale drum which thus rotates together with the driver element at least during dose setting.

In a further example, the driver element rotates back to its initial position during expelling of the set dose. Since the arms of the scale drum extend through the driver element this backwards rotation is also conveyed to the scale drum which thus rotates also during expelling of the set dose.

In such example, the scale drum thus rotates helically on the piston rod during dose setting since the piston rod is held inrotatable during dose setting. During expelling of the set dose, the piston rod screws forward in a helical movement which thus also brings along the scale drum in a helical movement back to its initial position.

Since the scale drum moves helically, the radial arms of the scale drum travels axially inside the injection device, this movement being accommodated by the longitudinal opening in the driver element.

When rotating the drive element in either rotational direction, the force is thus transformed to the scale drum by the abutment between the radial arms on the scale drum and the sidewalls of the longitudinal opening or slit in the driver element.

In a further aspect, the driver element is axially movable between a first position and a second position by the user activating an injection button which is coupled to the driver element.

An injection button which is preferably located at a proximal end of the pen-shaped injection is stiffly connected to the driver element such that the driver element moves in the distal direction when a pressure is applied to the injection button.

In one example a compression spring is provided which urges the injection button, and the driver element, back to the initial position when no pressure is applied to the injection button.

The driver element thus shifts between two different positions;

A first position wherein the driver element engages the dose setting member to rotate with the dose setting member. In this first position the driver element is rotationally de-coupled from the piston rod guide. By rotational de-coupled means that the driver element and the piston rod guide is able to rotate independently of each other, however, there can be some degree of physical overlapping of the elements without transferring rotation, and A second position in which the driver element is rotationally decoupled from the dose setting member. In this second position the driver element is rotational coupled to the piston rod guide such that the rotation of the driver element caused by the torsion spring is transformed to a rotation of the piston rod guide thereby driving the piston rod forward.

The piston rod guide is internally provided with a non-circular opening which engages the non-circular cross section of the piston rod such that the piston rod rotates whenever the piston rod guide is rotated. The piston rod further has a thread on the outside engaging a similar thread provided in the housing of the injection device (or in an element coupled to the housing) such that the piston rod is rotated forward whenever the piston rod guide is rotated.

The non-circular cross section of the piston rod can be shaped in many different ways. It can e.g. be a longitudinal groove or a track, or it can be provided by cutting away part of the circular cross section thus providing a flat longitudinal surface.

In the first position of the driver element (the dose setting mode) rotation of the dose setting member introduces a torque in the torsion spring which is operable and preferably also physical encompassed between, the driver element and the housing. The introduced torque is further released to drive an ejection upon movement of the driver element axially into the second position.

In the second position, the driver element has been moved axially to rotationally engage the piston rod guide such that the piston rod guide and the driver element rotate in unison.

The torsion spring can be pre-strained with a predetermined torque. If the user only dials a small dose, the torque introduced in the torsion spring during dose setting can in one example be too small to overcome the friction between the different rotatable elements in the injection device. It is therefore often seen that such torsion springs are prestrained such that the spring characteristic in the zero position of the injection device lies above the zero point of the spring force. Or in other words that torque is always present in the torsion spring even when the scale drum is in its zero position. When the prestrained torque overcomes the friction it is thus possible to eject even very small doses.

In the first position of the driver element, when the dose setting button and the driver element are rotated together, a torque is thus build up in the torsion spring. This torque needs to be maintained in the torsion spring also when the user removes the fingers from the dose setting button. A mechanism holding the torque of the strained torsion spring may thus be provided between the dose setting member and the housing, since the dose setting member is rotationally coupled to the driver element. The term housing is also meant to encompass a part connected to the housing.

The mechanism can be materialized in many different ways both axially or radially. It can be one or more radial ratchet arms being locked in one rotational direction against a toothed ring or it can be axially provided by opposed saw-teeth in an engagement e.g. established by a resilient force which can be delivered by a compression spring.

The torsion spring used can either be a helically wounded torsion spring or it can be a non-helical wounded clock spring. A non-helical spring requires only very little axial space inside the housing, whereas a helical spring does not require much radial space.

In a different aspect, the housing of the pen-shaped injection device is formed as a unitary tubular housing element which surrounds at least the scale drum, the torsion spring and a majority of the cartridge. The unitary housing thus has an axial length such that both the dose mechanism and the majority of the cartridge are contained inside the unitary housing. This makes the assembly of the injection device very simple. The dose mechanism can be loaded into the unitary housing element from one end and the cartridge can be loaded into the other end of the unitary housing element. The compartment of the unitary housing containing the cartridge can be separated from the compartment holding the dose mechanism by a partition which is only penetrated by the piston rod.

By the majority of the cartridge is meant that more than 50% and preferably more than 80% of the cartridge.

In one example, the unitary housing part is sealed at the distal end by a capsule-formed element carrying the interface for holding the injection needle. In such example nearly the entire cartridge must be contained in the unitary housing such that the capsule-formed part can be connected to the unitary housing part. The connection can be established by a click-fit, a press-fit or the capsule-formed part can be glued or welded to the unitary housing part. In one example, a capsule-formed part extends only to the shoulders of the cartridge.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Injection Needle" is used to describe an assembly made form a hub holding the actual conduit performing the penetration of the skin during injection. The actual conduit is often referred to as the "Needle Cannula" and is usually made from a metallic material such as e.g. stainless steel. A needle cannula could however also be made from a polymeric material or a glass material. The hub also carries the connecting means for connecting the injection needle to an injection apparatus and is usually moulded from a suitable thermoplastic material. The "connection means" could as examples be a luer coupling, a bayonet coupling, a threaded connection or any combination thereof e.g. a combination as described in EP 1,536,854.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

"Scale drum" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols. These symbols are preferably, but not exclusively, Arabian numbers from "0" to "9". In a traditional injection pen configuration the indicia is viewable through a window provided in the housing.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 9A shows an exploded view of a third embodiment.

FIG. 9B shows an enlarged view of the drive assembly of FIG. 9A

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and usually carrying the dose dial button.

Distal and proximal are meant to be along an axial orientation extending along the longitudinal axis of the injection device and is further indicated in the figures.

Figure 1:
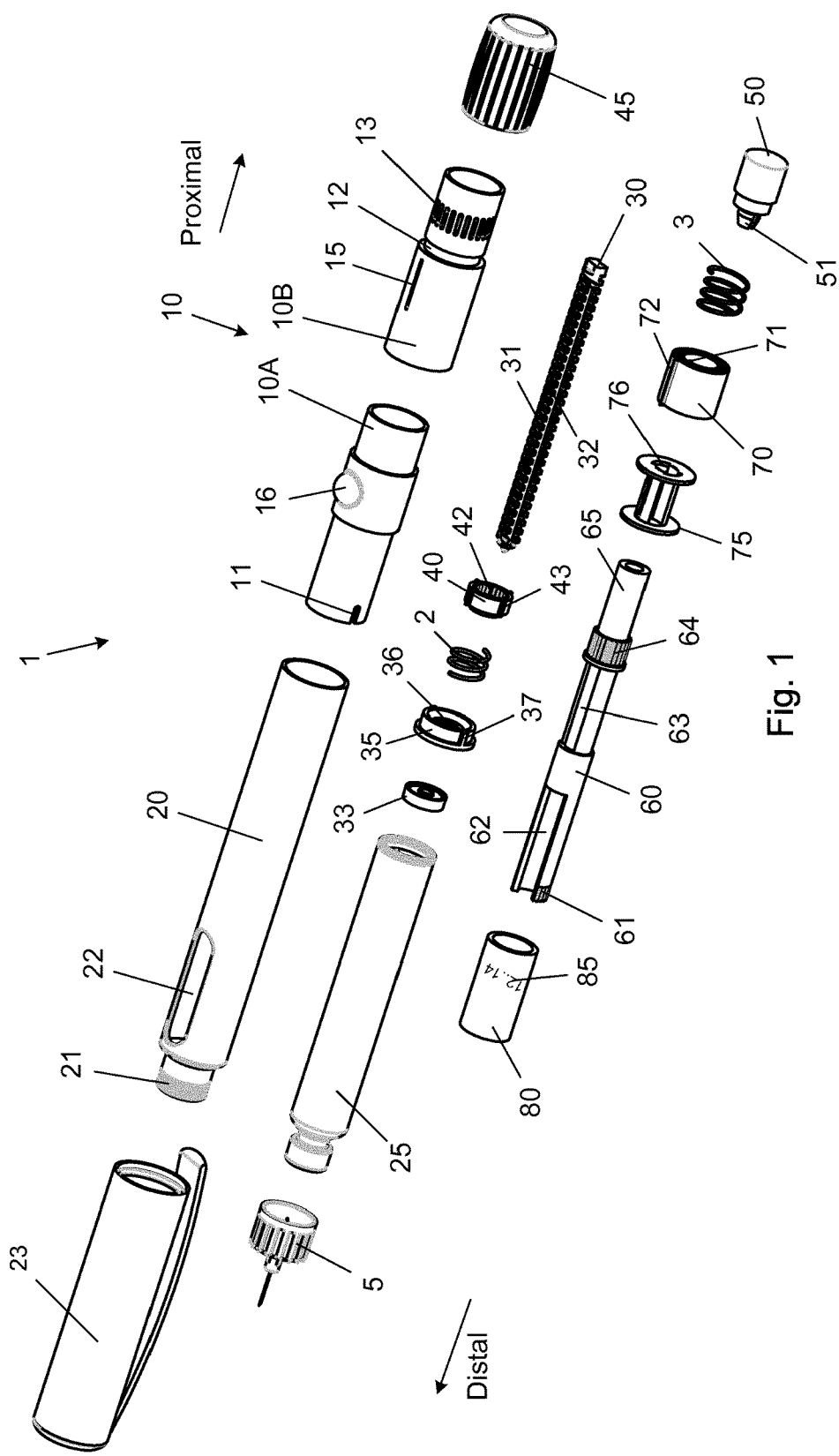
FIG. 1 shows an exploded view of a first embodiment of an injection device.
Figure 2:
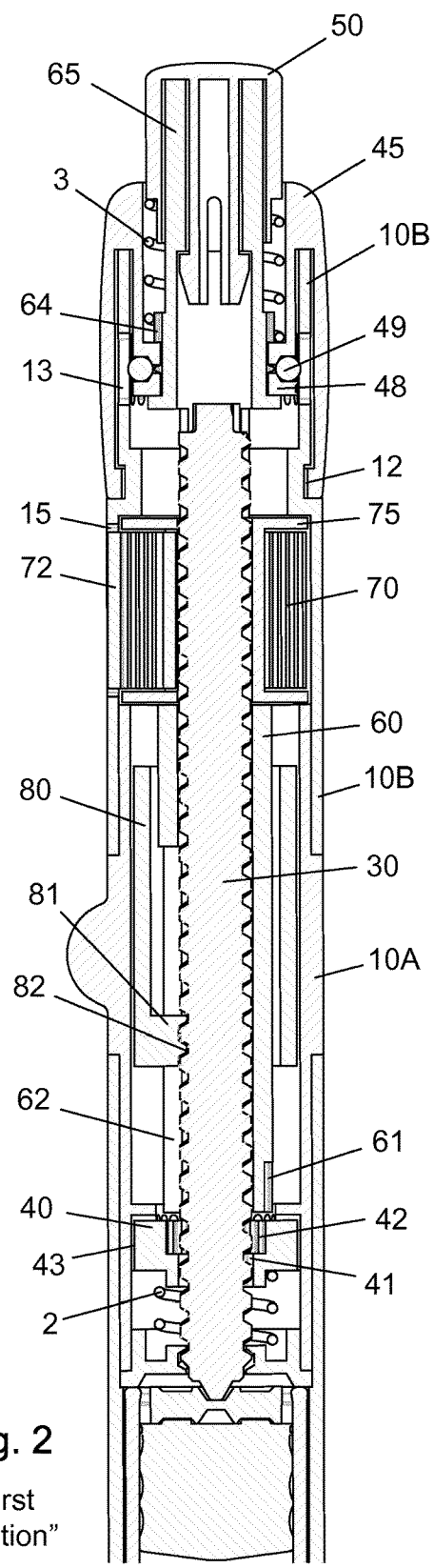
FIG. 2 shows a cross-sectional view of the injection device of FIG. 1 in the first position.
Figure 3:
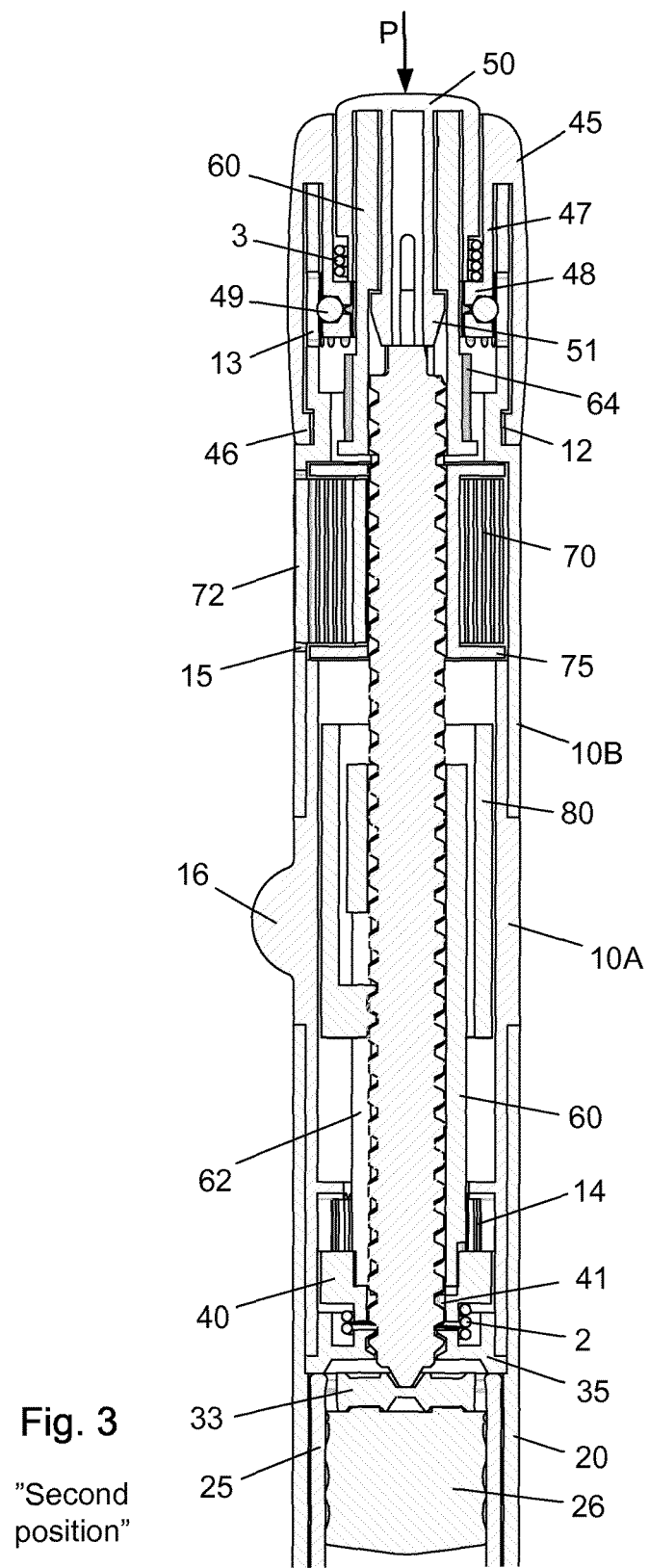
FIG. 3 shows a cross-sectional view of the injection device of FIG. 1 in the second position.

First Embodiment—FIGS. 1 to 3

FIG. 1 depicts an exploded view of the torsion spring operated and pen-shaped injection device 1 according to a first embodiment. The outer shell is made up from a housing 10 which is divided into a distal housing part 10A and a proximal housing part 10B. The distal housing part 10A is attached to a cartridge holder 20 which holds the cartridge 25 containing the liquid drug.

A cartridge holder 20 is preferably irreversible connected to the distal housing part 10A thus making the injection device a so-called pre-filled injection device. The cartridge holder 20 is distally provided with a thread 21 (or a similar connection mean) for attaching an injection needle 5 to the injection device. Further, the cartridge holder 20 is equipped with a window 22 through which the liquid drug contained in the cartridge 25 can be inspected.

In order to protect the liquid drug from exposure to daylight during storing of the injection device 1, a removable cap 23 is mounted on the outside of the cartridge holder 20 thus covering the window 22.

The cartridge 25 is further provided with a movable plunger 26 which is moved forward by a piston rod 30. This piston rod 30 is provided with an outside thread 31 and a longitudinal groove 32. In order to equally distribute the force from the piston rod 30 to the plunger 26 a piston rod foot 33 is provided between the piston rod 30 and the plunger 26.

The outside thread 31 of the piston rod 30 is threaded to a similar thread 36 provided internally in a nut member 35. This nut member 35 is rotational secured to the distal housing part 10A, or alternatively moulded as an integral part of the distal housing part 10A. In order to secure the depicted nut member 35 to the housing 10, the nut member 35 is provided with a longitudinal tongue 37 which engages a longitudinal slit 11 in the distal housing part 10A.

Whenever the piston rod 30 is rotated it moves forward due to the engagement between the outside thread 31 of the piston rod 30 and the internal thread 36 of the nut member 35.

In order to rotate the piston rod 30, a piston rod guide 40 is provided. This piston rod guide 40 is internally and distally provided with at least one key 41 engaging the longitudinal track 32 of the piston rod 30 such that the piston rod 30 rotates whenever the piston rod guide 40 is rotated. Proximally, the piston rod guide 40 is internally provided with a toothed ring 42 and on the outside surface a number of longitudinal tongues 43 are provided the purpose of which will be explained later.

The piston rod guide 40 is urged in the proximal direction by a first compression spring 2 which is encompassed between the nut member 35 and the piston rod guide 40. In the first position depicted in FIG. 2 which is the situation during dose setting, the piston rod guide 40 is positioned in its most proximal position and the longitudinal tongues 43 are rotational locked in similar tracks 14 (see FIG. 3) provided internally in the distal housing part 10A.

At the proximal end of the injection device 1, the proximal housing part 10B carries a dose setting button 45. This dose setting button 45 has a rim 46 engaging a groove 12 provided externally on the proximal housing part 10B. Further, the dose setting button 45 is provided with an extension 47 which extend on the inside surface of the second housing part 10B. Distally this extension 47 is provided with an inwardly pointing part 48 which carries a number of balls 49.

This inwardly pointing part 48 is on its inside surface provided with means such as teeth to engages with the toothed ring 64 on the drive element 60 whenever the injection device 1 is in its first position as seen in FIG. 2.

As can be best seen in FIG. 1, the proximal housing part 10B has a number of slits 13 which internally supports the balls 49.

The balls 49 are secured to the inwardly pointing part 48 of the dose setting button 45 such that whenever the user rotates the dose setting button 45 to set a dose, the balls 49 also rotate against the slits 13. The dose setting button 45 is thus rotatable in one direction to set a dose and in the opposite direction to decrease a set dose.

The dose setting button 45 is further provided with a proximal opening through which the injection button 50 extends. The injection button 50 is via a flexible grip 51 secured to the drive member 60. Further, a second compression spring 3 is provided between the injection button 50 and the inwardly pointing part 48 of the dose setting button 45 urging the injection button 50 in the proximal direction.

When the injection button 50 is not activated as in FIG. 2, i.e. during dose setting, the second compression spring 3 via the injection button 50 urges the driver element 60 in the proximal direction.

The driver element 60 which is best viewed in FIG. 1 is distally provided with a toothed interface 61. Further, the distal part of the driver element 60 has an open longitudinal slit 62. The centre part of the driver element 60 is provided with a longitudinal groove 63 and proximal to the centre part, the driver element 60 is provided with a toothed ring 64 and a proximal extension 65.

In the dose setting mode as depicted in FIG. 2, the driver element 60 is moved in the proximal direction by the second compression spring 3 such that the toothed interface 61 is located proximal to the toothed ring 42 of the piston rod guide 40. The driver element 60 is thus rotatably independently of the piston rod guide 40. In this first position, the piston rod guide 40 is rotational locked to the housing 10 by having its external tongues 43 engage the tracks 14 provided in the distal housing part 10B.

Further, in the dose setting mode (first position), the inwardly pointing part 48 of the dose setting button 45 engages the toothed ring 64 such that rotation of the dose setting button 45 is conveyed to a simultaneous rotation of the driver element 60.

A clock spring 70 dedicated to drive the driver element 60 is depicted in FIG. 1. This clock spring 70 is a torsion spring embodied in this embodiment as a clock-spring 70, which is a wounded spring not having any particular axial extension but wounded in one dimension only i.e. having no helical coils. Such clock-springs are usually wounded from a metal strip having a certain width. The number of wounds and the width are important factors determining the torque applied by such clock spring 70.

The inner winding has an inwardly pointing flange 71 securing the clock spring 70 to a spring base 75, and the outer winding has a similar fold 72 securing the spring 70 to the proximal housing part 10B by being inserted into a longitudinal groove 15 in the housing wall.

The spring base 75 is on its inside surface provided with a tongue 76 which engages the longitudinal groove 63 of the driver element 60 such that the spring base 75 and the driver element 60 rotate together. However, the driver element 60 is able to slide relatively to the spring base 75 such that the driver element 60 can be moved axially during dosing.

When setting a dose to be injected, the user holds the device as in FIG. 2, i.e. without pressing the injection button 50. In this position, the user rotates the dose setting button 45. Due to engagement between the inwardly pointing part 48 of the dose setting button 45 and the toothed ring 64 of the driver element 60, the driver element 60 is also rotated.

The spring base 75 follows the rotation of the driver element 60 thus straining the torsion spring 70. The engagement between the balls 49 (secured to dose setting button 45) and the slits 13 of the housing 10 prevents the torque of the torsion spring 70 from rotating the driver element 60 back to its initiate position, i.e. the torque is held by this engagement.

At the same time the piston rod 30 is secured against rotation by the engagement of the piston rod guide 40 with the housing via the engagement between the tracks 14 of the distal housing part 10A and the longitudinal tongues 43 provided externally on the piston rod guide 40.

As the driver element 60 is rotated, this rotation is conveyed to the scale drum 80 by the engagement between the open slit 62 on the driver element 60 and an inwardly pointing part 81 provided on the scale drum 80 as here explained.

The scale drum 80 is, as depicted e.g. in FIG. 2, provided with a part 81 pointing inwardly. This part 81 carries a thread 82 which mates the thread 31 of the piston rod 30 such that the scale drum 80 moves helically when rotated in relation to the piston rod 30.

As a result, whenever the driver element 60 is rotated the scale drum 80 also rotates and is forced to move helically such that indicia 85 printed, or otherwise provided, on the scale drum 80 passes by a window 16 in the housing 10. This window 16 is preferably provided with a magnifying lens magnifying the indicia 85.

To inject the set dose, the user activates the injection button 50 as indicated by the arrow "P" in FIG. 3. This movement also shots the driver element 60 axially forward such that the toothed interface 61 at the distal end of the driver element 60 engages the toothed ring 42 inside the piston rod guide 40. As the piston rod guide 40 is moved forward against the force of the first compression spring 2 and into the position depicted in FIG. 3, the longitudinal tongues 43 on the piston rod guide 40 moves out of engagement with the tracks 14 of the housing 10 and the piston rod guide 40 is thus set free to rotate. At the same time, the toothed ring 64 on the driver element 60 moves out of engagement with the inwardly pointing part 48 of the dose setting button 45. In this position, the clock spring 70 rotates the driver element 60 which in turn also rotate the piston rod guide 40 which again rotate the piston rod 30. Whenever the piston rod 30 is rotated it is screwed forward in the thread 36 fixed in relation to the housing 10 and is thus moved further into the cartridge 25.

The sequence is thus that the driver element 60 is moved into engagement with the piston rod guide 40 which is at the same time is moved axially out of its engagement with the tracks 14 of the housing 10. At the same time, the driver element 60 is moved out of its engagement with the dose setting button 45 by moving the toothed ring 64 of the driver element 60 out of engagement with the inwardly pointing part 48 of the dose setting button 45.

During dose setting; the dose setting button 45, the drive element 60 and the scale drum 80 rotate together while the clock spring 70 is being strained.

During injection, the driver element 60, the piston rod guide 40, the scale drum 80 and the piston rod 30 is rotated together by the force accumulated in the clock spring 70. As the piston rod 30 is screwed forward in the thread 36, the scale drum 80 threadedly engaging the piston rod 30 returns to its initial position.

Second Embodiment—FIGS. 4 to 8

Figure 4:
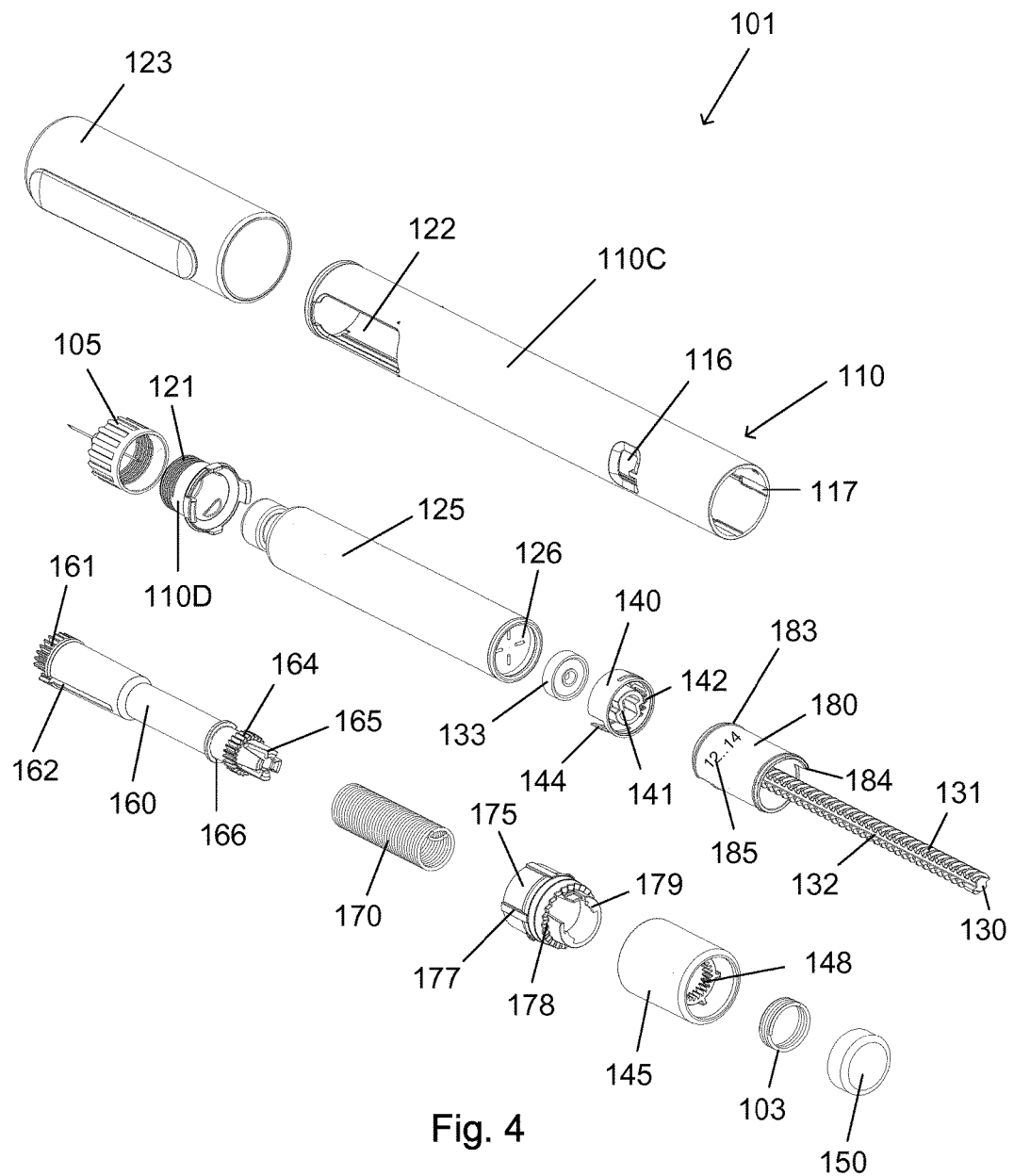
FIG. 4 shows an exploded view of a second embodiment.

A second embodiment is disclosed in the FIGS. 4 to 8. FIG. 4 disclose an exploded view of this second embodiment wherein similar elements are numbered by the same reference number as in the first embodiment, however with a "1" in front.

The housing 110 is in this second embodiment divided into a main housing part 110C and a distal housing part 110D. The distal housing part 110D is secured to the main housing part 110C after a cartridge 125 has been placed inside the main housing part 110C.

The distal housing part 110D carries a thread 121 securing the injection needle 105 and the main housing part 110C holds both the cartridge 125 and the dose mechanism. The main housing part 110C is further provided with a longitudinal window 122 through which a user can inspect the liquid drug contained inside the cartridge 125.

The main housing part 110C has a length such that it can contain both the dose mechanism and at least the majority of the cartridge 125. In fact, the distal housing part 110D is shaped as a capsule that it clicked onto the main housing part 110C during assembly of the injection device 101.

Figure 5A:
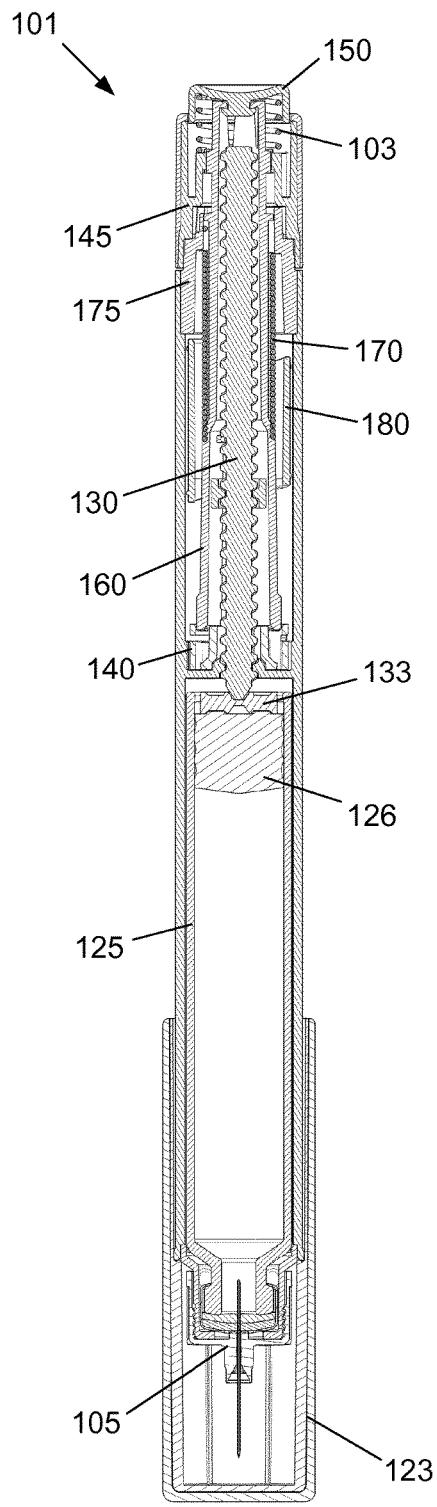
FIG. 5A-B show a cross sectional view of the injection device from FIG. 4 in the first position.

The distal part of the injection device 101 including the longitudinal window 122 is, when not in use, covered by a removable cap 123 as e.g. disclosed in FIG. 5A.

The cartridge 125 is a well-known glass cartridge 125 which proximally is provided with a plunger 126 which can be moved in the distal direction by a piston rod 130.

The piston rod 130 has an external thread 131 and a longitudinal groove 132. Distally the piston rod 130 abuts a piston rod foot 133 which transfers the force from the piston rod 130 to the plunger 126 over an enlarged area.

The longitudinal groove 132 of the piston rod 130 is further engaged by a piston rod guide 140 which internally is provided with a key 141 to engage the longitudinal groove 132 of the piston rod 130. Rotation of the piston rod guide 140 is thus transferred to rotation of the piston rod 130 which again is screwed forward in a thread 136 provided in the main housing part 110C. The thread 136 could also be provided in a nut member coupled to the main housing part as in the first embodiment.

Internally the piston rod guide 140 is provided with teeth 142 engageable to the driver element 160. Externally the piston rod guide 140 is provided with one or more ratchet arms 144 which engage a toothed interior 118 of the main housing part 110C such that the piston rod guide 140 can only rotate in one rotational direction. It is thus not possible to move the piston rod 130 in the proximal direction.

The main housing part 110C is further provided with a window 116 through which a user is able to view indicia 185 provided on the scale drum 180. This window 116 can in one aspect be an opening in the main housing part 110C or alternatively it can be covered by a transparent element. As in the first embodiment, this transparent element can be a magnifying lens for magnifying the indicia 85.

The scale drum 180 is internally provided with a number of inwardly pointing arms 181 (see FIG. 7-8) which carries a thread 182 mating the outside thread 131 of the piston rod 130. Externally the scale drum 180 can be provided with circumferential ridges 183 which slide on an internal surface of the main housing part 110C to reduce friction.

The inwardly pointing arms 181 of the scale drum 180 protrude through a pair of open slits 162 provided in the driver element 160. Distally the drive element 160 is provided with a toothed interface 161 whereas the proximal half is provided with a toothed ring 164. Most proximal the driver element 160 is provided with a plurality of flexible arms 165 securing the injection button 150.

The injection button 150 is urged in the proximal direction by a second compression spring 103 which is encompassed between the injection button 150 and the dose setting button 145.

The dose setting button 145 is internally provided with radially pointing teeth 148 for engaging the toothed ring 164 of the driver element 160 as explained later. On the outside surface, the dose setting button 145 is provided with a soft rubber layer 190 which is preferably moulded onto the dose setting button 145 using a 2K moulding technic.

The main housing part 110C is proximally closed by a spring base 175 which has a plurality of longitudinal notches 177 engaging longitudinal slits 117 provided on the inside surface of the main housing part 110C. The spring base 175 thus operational functions as an integral part of the main housing part 110C and could in an alternative be moulded as an integral part of the main housing part 110C.

The spring base 175 is further proximally provided with internally pointing flange parts 179 which rest against an outwardly pointing flange 166 provided on the driver element 160. This engagement prevents the driver element 160 from moving proximally and also helps transferring the force of the second compression spring 103 onto the dose setting button 145.

The spring base 175 secures the proximal end of a torsion spring 170 having its distal end secured to the driver element 160 to drive an injection. The torsion spring 170 disclosed in this embodiment is a well-known helically wounded torsion spring 170.

The toothed ring 164 of the driver element 160 engages the radial teeth 148 of the dose setting button 145 such that rotation of the dose setting button 145 is transferred to a rotation of driver element 160, which rotation strains the torsion spring 170. As best seen in FIG. 4, the radial teeth 148 are provided on a bridge which also functions as a torque limiter allowing the dose setting button 145 to continue rotation even if the driver element 160 comes to a stop.

In order to maintain the torque in the torsion spring 170 when the dose setting button 145 is not rotated, a plurality of axially pointing teeth 149 provided internally in the dose setting button 145 is urged axially against a toothed ring 178 provided proximally on the spring base 175.

Figure 5B:
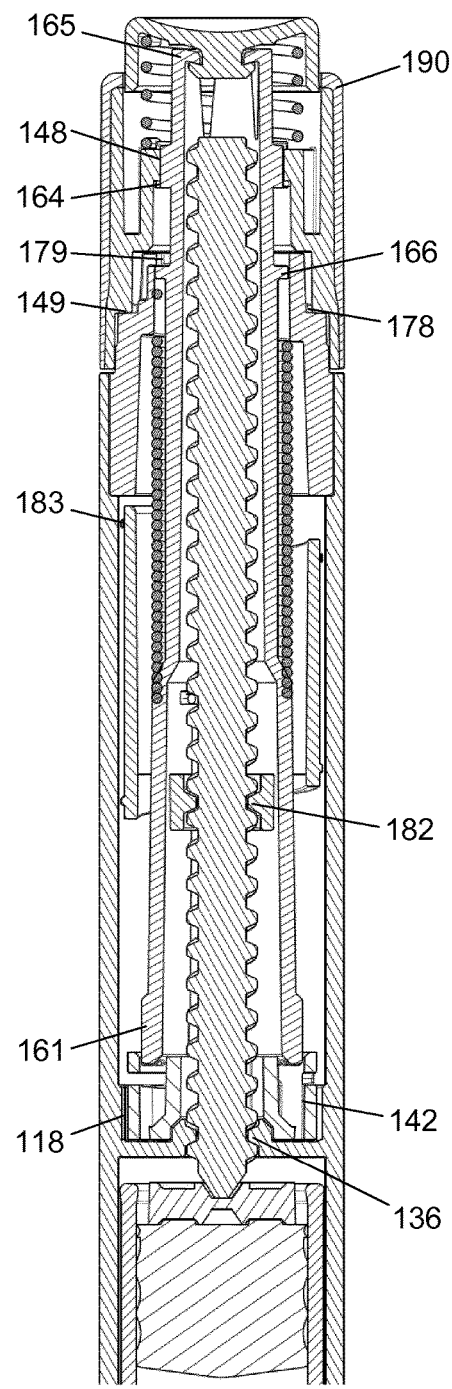

When a dose is to be set, the injection device 101 is held in the first position as depicted in FIG. 5 where FIG. 5A depict the full injection in the first position and FIG. 5B discloses a partial enlarged view of the dose mechanism of FIG. 5A.

In the first position rotation of the dose setting button 145 is transferred to rotation of the drive element 160 which is positioned in its proximal position due to force of the second compression spring 103.

The driver element 160 is coupled to the dose setting button 145 by the toothed engagement between the internal radial teeth 148 of the dose setting button 145 and the toothed ring 164 on the driver element 160. The toothed interface 161 is at the same time axially removed from the internal teeth 142 of the piston rod guide 140 by the second compression spring 103 pulling the driver element 160 in the proximal direction.

When the driver element 160 is rotated in the dose setting direction, the torsion spring 170 is strained, and when rotated in the opposite direction, the torsion spring 170 is released. The engagement between the axially pointing teeth 149 and toothed ring 178 secures that the torque is maintained in the torsion spring 170 also when the user removes the fingers from the dose setting button 145.

When the correct dose has been dialed, the user releases the set dose by pushing the injection button 150 in the distal direction against the force of the second compression spring 103.

Figure 6A:
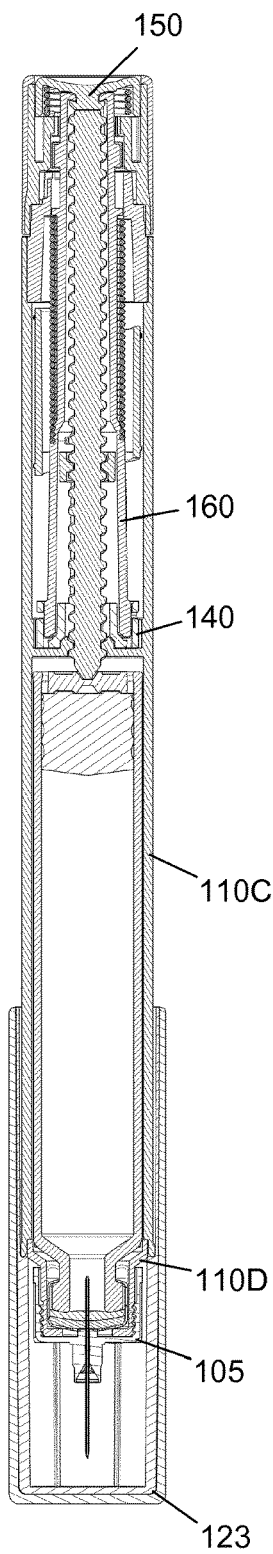
FIG. 6A-B show a cross sectional view of the injection device from FIG. 4 in the second position.
Figure 6B:
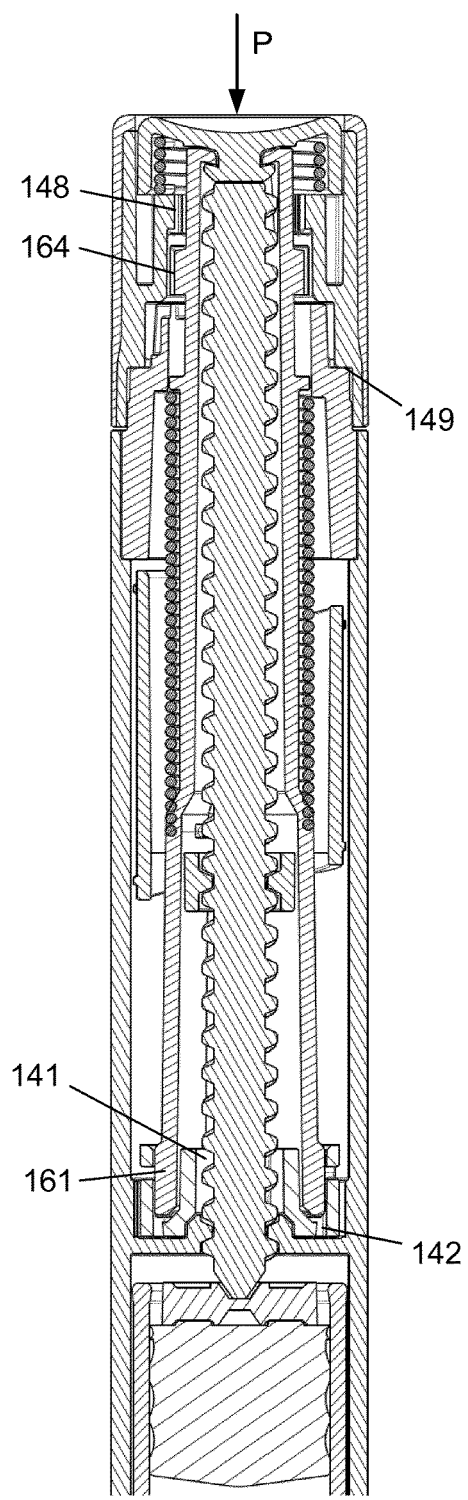

This second position is depicted in FIG. 6, where FIG. 6A is a full picture of the injection device 101 and FIG. 6B is a partial end enlarged view of the dose mechanism of FIG. 6A.

Movement of the injection button 150 in the distal direction as indicated by the arrow "P" in FIG. 6B is immediately transferred to an axial movement of the driver element 160. When the driver element 160 is moved in the distal direction the toothed ring 164 slides out of engagement with the radial teeth 148 of the dose setting button 145 where after the driver element 160 is forced to rotate by the torque present in the torsion spring 170.

At the same time the toothed interface 161 distally on the driver element 160 is moved into engagement with the teeth 142 of the piston rod guide 140 such that the piston rod guide 140 is forced to rotate together with the driver element 160.

Rotation of the piston rod guide 140 translates to rotation of the piston rod 130 which henceforth moves in the distal direction while pressing the plunger deeper into the cartridge 125.

FIG. 5 and FIG. 6 both disclose the injection device 101 with the scale drum 180 in the maximum position i.e. the maximum dose of the injection device 101 is set. In this maximum position a stop flange 184 on the scale drum 180 abut a similar stop provided on the spring base 175.

Figure 7:
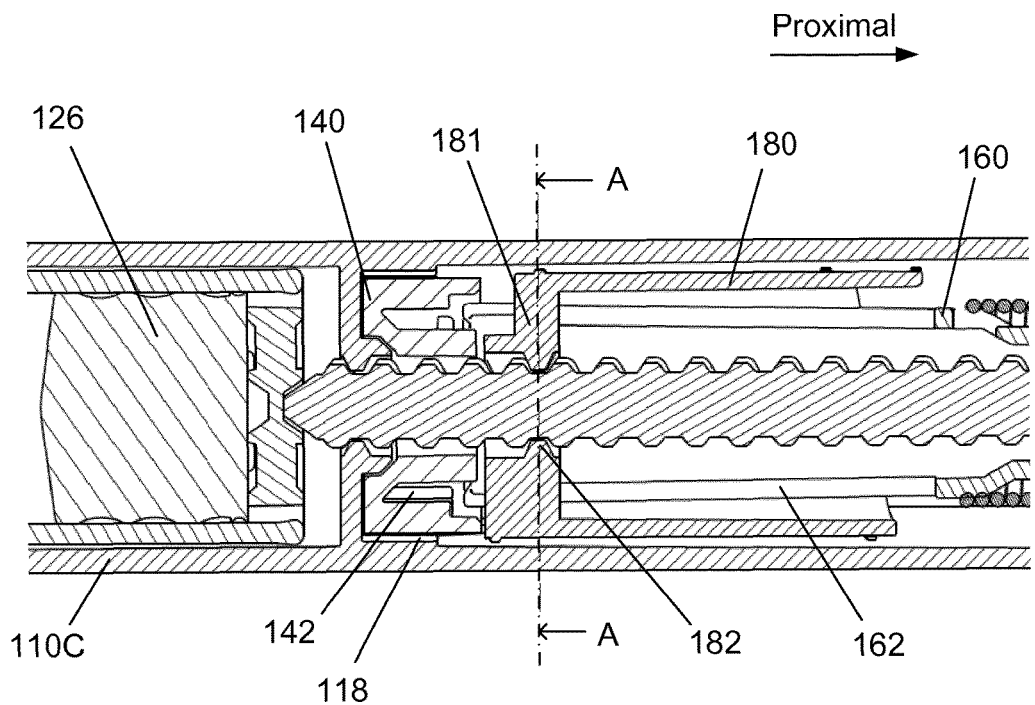
FIG. 7 show an enlarged view of the injection device from FIG. 4.
Figure 8:
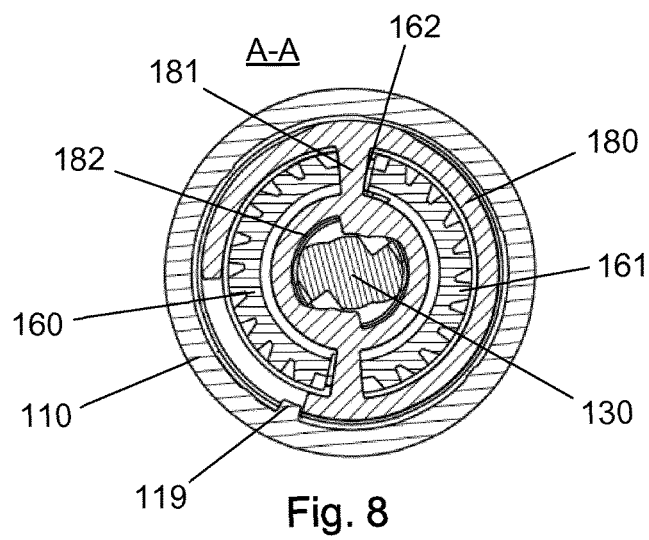
FIG. 8 Show a cross sectional view through the line A-A in FIG. 7.

FIG. 7 discloses the scale drum 180 when it has returned to the zero position after having expelled the set dose. In this position a distal stop flange on the scale drum 180 abut a stop 119 provided internally in the housing 110 as seen in FIG. 8.

In FIG. 7, the injection button 150 is not activated, and the driver element 160 is thus positioned in the proximal position i.e. not coupled to the piston rod guide 140.

The sequence in this embodiment thus being that the piston rod guide 140 does not move axially at all, but the driver element 160 is moved axially into contact with the piston rod guide 145 as the drive element 160 is moved out of engagement with the dose setting button 145. With the driver element 160 in the first position (FIG. 5), the piston rod guide 140 is able to rotate in one direction since the piston rod guide 140 is not locked to the housing 110. However, the piston rod guide 140 is prevented from rotation in a rotational direction that would cause the piston rod 130 to move in the proximal direction i.e. the piston rod 130 can only move in the distal direction (the dose expelling direction). The one-way rotational lock is due to the engagement between the ratchet arms 144 on the piston rod guide 140 and the toothed interior 118 of the housing 110.

When setting a dose in the first position, rotational force is transmitted from the driver element 160 to the scale drum 180 by the engagement of the open slit 162 with the inwardly pointing part 181 of the scale drum 180. The internal thread 182 of the scale drum 180 secures that the scale drum 180 engages the outer thread 131 of the piston rod 130 such that the scale drum 180 is moved helically up and down the piston rod 130.

When the set dose is expelled, the driver element 160 rotate in the opposite direction, however the engagement between the open slit 162 of the driver element 160 and the inwardly pointing part 181 of the scale drum 180 secures that the scale drum 180 move helically back to its initial position.

Third Embodiment—FIGS. 9 to 13

Yet another embodiment is disclosed in the FIGS. 9 to 13 where FIG. 9A disclose an exploded view of the third embodiment wherein similar elements are numbered by the same reference number, however with a "2" in front.

As can be seen from the figures, the cartridge 225 is secured in a housing 210 which in this third embodiment is divided into a main housing part 210C and a distal housing part 210D. The distal housing part 210D is secured to the main housing part 210C after the cartridge 225 has been placed inside the main housing part 210C e.g. by gluing the two parts 210C-D together.

The distal housing part 210D carries the thread 221 securing the injection needle 205 and the main housing part 210C holds both the cartridge 225 and the dose mechanism. The distal part of the injection device 201 is, when not in use, covered by a removable cap 223 as disclosed in FIG. 10A.

In the third embodiment, the driver element 260 is divided into a distal driver part 260A and a proximal driver part 260B. These two driver parts 260A-B are secured to each other such that they both rotate and translate axially together as one unison driver element 260. Distally, this driver element 260 is connected to the torsion spring 270 which again proximally is connected to the spring base 275.

The spring base 275 is coupled to the housing 210 or alternatively moulded as an integral part of the housing 260. The result being that whenever, the driver element 260 is rotated to set a dose, the torsion spring 270 is strained.

In order to rotate the driver element 260 during dose setting, the driver element 260 is coupled to the dose dial button 245. This coupling is in the third embodiment an axial coupling between a toothed ring 264 on the driver element 260 and axially placed internal teeth 248 provided inside the dose setting button 145. A second compression spring 203 urges the internal teeth 248 against the toothed ring 264. The force of the second compression spring 203 together with the coupling also functions as a torque limiter since the coupling (264/248) is able to slide if a user keeps rotating the dose setting button 245 after the driver element 260 has come to a stop. However, if the torque is not surpassed, the driver element 260 rotates together with the dose setting button 245 during dose setting.

To stabilize the driver element 260 a stabilizer ring 267 is surrounding the driver element 260. At its distal end, the driver element 260 (the distal driver part 260A) is further provided with an axially pointing toothed interface 261 which engages a drive assembly 255.

The drive assembly 255 comprises the piston rod guide 240, a spring 256 and a toothed drive ring 257. The teeth 242 on this toothed drive ring 257 points in an axial direction. Both the spring 256 and the toothed driver ring 257 are coupled to the piston rod guide 240 to rotate with the piston rod guide 240. The toothed drive ring 257 is internally provided with a shape configured to rotational lock to a similar shape provided in the piston rod guide 240 and the spring 256 is further provided with bended arms 258 which lie against a surface of the piston rod guide 240. The result being that both the toothed driver ring 257 and the spring 256 rotate together with the piston rod guide 240 which again is secured to the driver element 260 by a number of hooks 259 engaging the driver element 260 such that the drive assembly 255 including the piston rod guide 240 moves axially together with the driver element 260 as will be explained later.

The bended arms 258 of the spring 256 further engages a toothed interior 218 of the housing 210 such that the drive assembly 255 can only rotate in one rotational direction, however in the first position depicted in FIG. 10, the piston rod guide 240 (and thus the drive assembly 255) is prevented from rotation also in the opposite direction by the engagement between the external teeth 243 on the piston rod guide 240 and the tracks 214 provided internally in the housing 210.

Figure 10A:
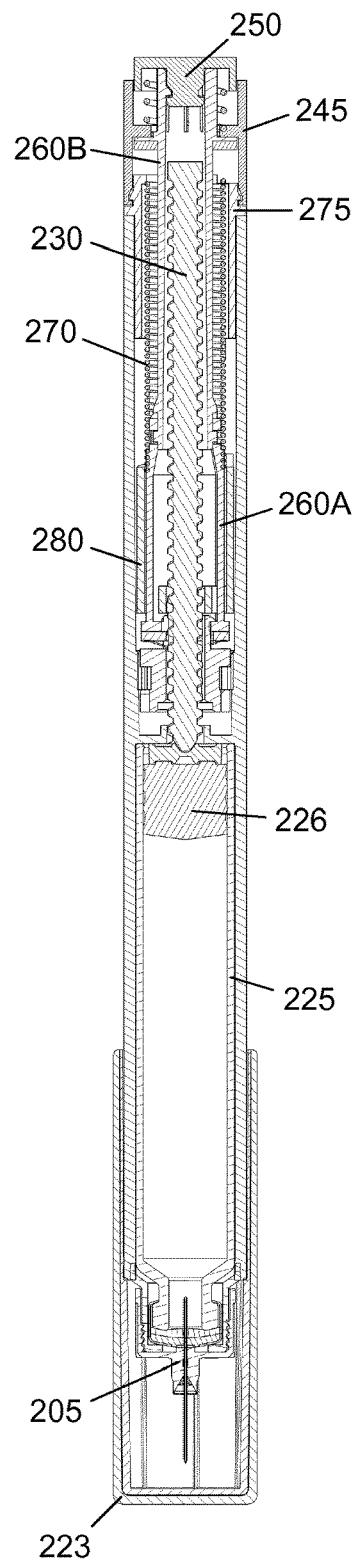
FIG. 10A-B show a cross sectional view of the injection device from FIG. 9 in the first position.
Figure 10B:
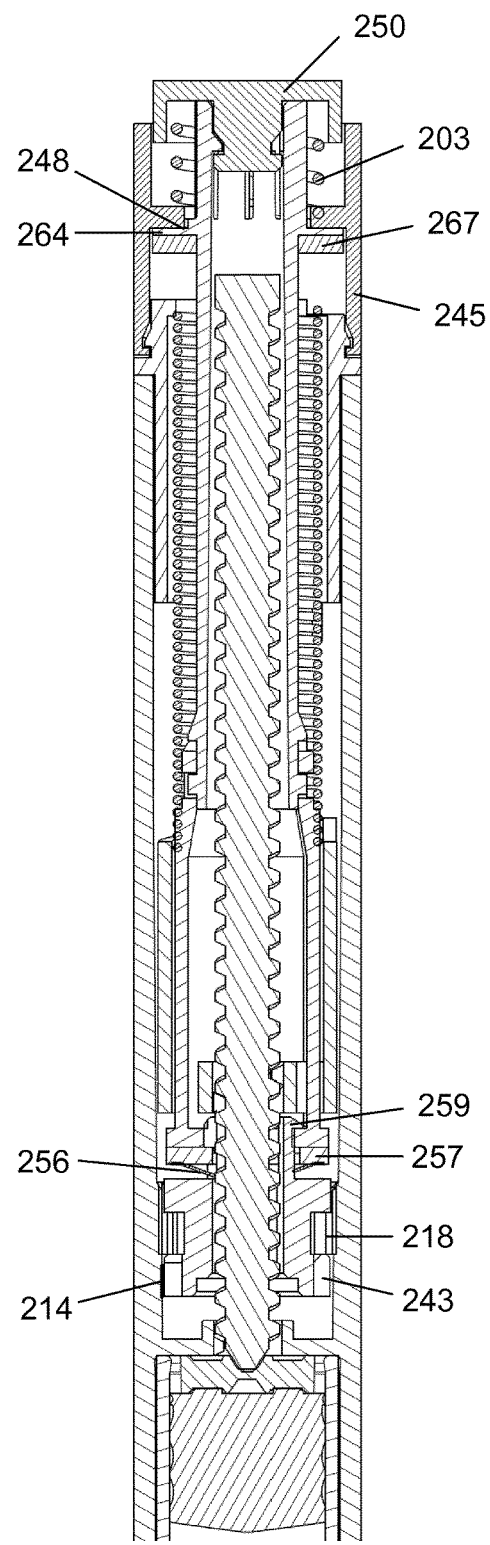

The first position is disclosed in FIG. 10 where FIG. 10A disclose the entire injection device 201 and FIG. 10B disclose an enlarged view of the dose mechanism. In operation, the user selects a dose to be injected by rotating the dose setting button 245. This rotation is conveyed to a similar rotation of the driver element 260 thus straining the torsion spring 270.

The piston rod guide 240 is secured against rotation by the external teeth 243 being rotational locked to the internal tracks 214 inside the housing 210. Since the piston rod guide 240 is prevented form rotation so is the toothed driver ring 257 and the toothing 242 provided on the toothed driver ring 257 clicks over the distal toothing 261 on the driver element 260 thus providing the user with a clicking sound during dose setting.

As the user rotates the dose setting button 245 and the driver element 260 during dose setting, the torsion spring 270 encompassed there between is strained and the scale drum 280 move helically in the proximal direction.

Since the spring 256 urges the toothed drive ring 257 in the proximal direction, the engagement between the teeth 242 on the toothed drive ring 257 and the axial pointing teeth 161 on the driver element 160 secure that the torque is maintained in the torsion spring 270 until the torsion spring 270 is released to drive the driver element.

The connection between the driver element 260 and the scale drum 280 is disclosed in details in FIG. 7 and FIG. 8 which disclose the scale drum 280 returned to its zero position. The scale drum 280 carries an internal thread 282 threaded to the thread 231 of the piston rod 230. The part 281 of the scale drum 280 connecting the outer surface of the scale drum 280 and the thread 282 is engaged by the longitudinal slit 262 in the distal part 260A of the driver element 260. Henceforth when the driver element 260 is rotated, the scale drum 280 is also rotated.

During dose setting the external teeth 243 of the piston rod guide 240 is locked by the tracks 214 provided inside the housing 210 thus the drive assembly 255 is not rotated.

Figure 11A:
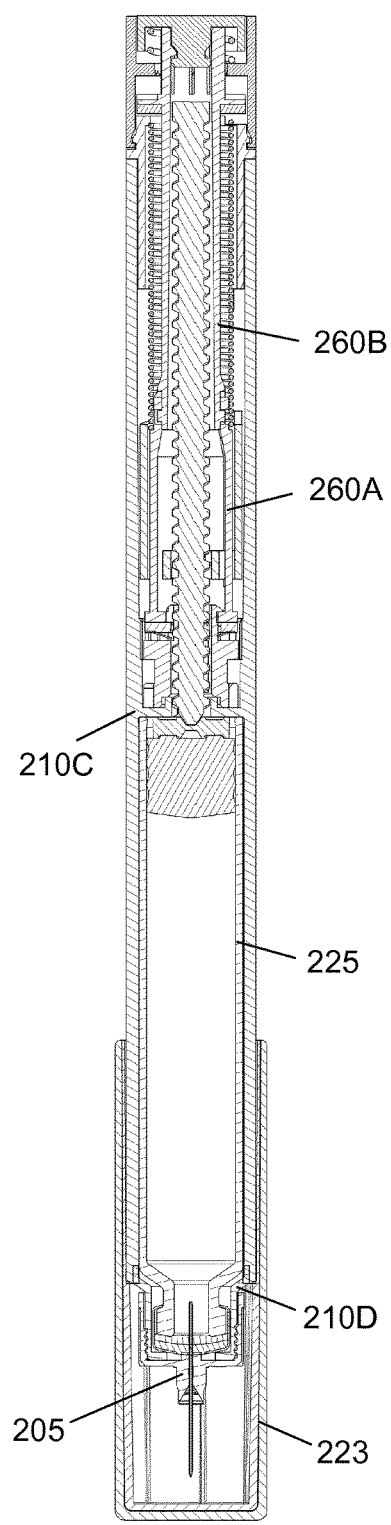
FIG. 11A-B show an enlarged view of the injection device from FIG. 9 in the second position.
Figure 11B:
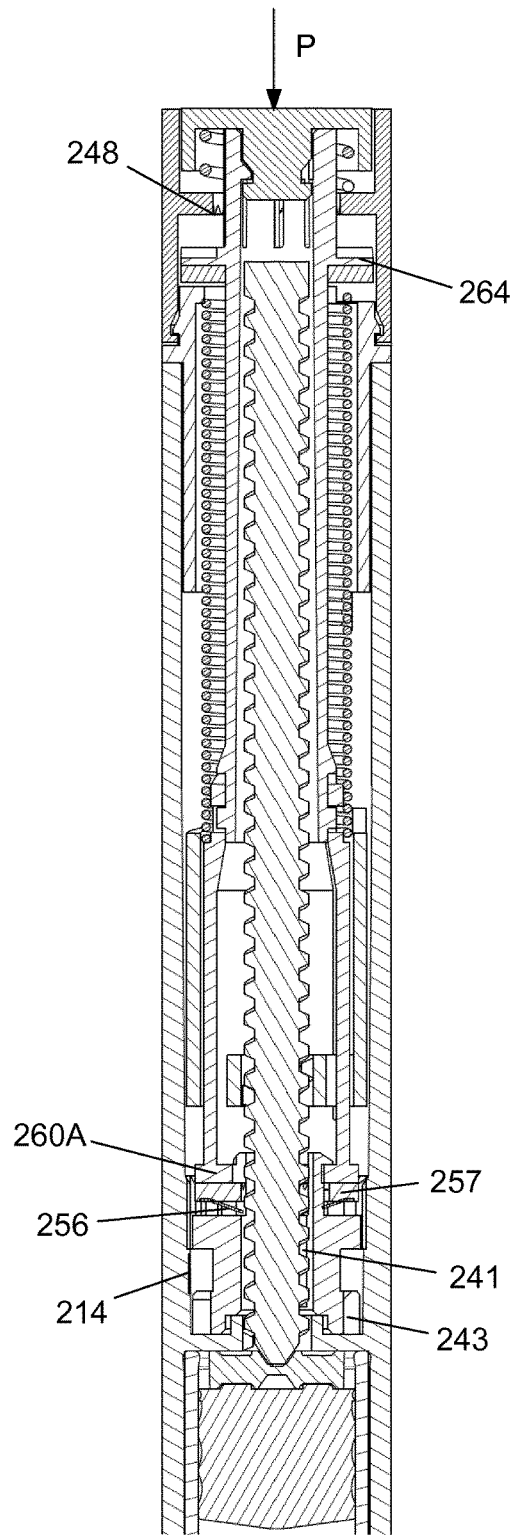

During dose expelling, the user pushes the injection button 250 in the distal direction as indicated by the arrow "P" in the FIGS. 11A-B where FIG. 11B is an enlarged view of the dose mechanism of FIG. 11A.

Proximally in the injection device 201 this movement moves the toothed ring 264 out of engagement with the internal teeth 248 such that the driver element 260 is able to rotate independently of the dose setting button 245.

Distally in the injection device, the external teeth 243 are moved out of the engagement with the internal tracks 214 inside the housing 210. Further, the toothed interface 261 is pressed against the teeth 242 on the toothed driver ring 257 whereby rotation of the driver element 260 is transformed to rotation of the toothed driver ring 257 and thus rotation of the piston rod guide 240 since the toothed driver ring 257 internally is shaped to fit the piston rod guide 240.

As in the previous embodiment, the piston rod guide 240 is internally provided with a key 241 which engages the longitudinal groove 232 in the piston rod 230 such that rotation of the drive assembly 255 and thus the piston rod guide 240 is transferred to a rotation of the piston rod 230.

A partition provided internally in the housing 210 is provided with a thread 236 such that rotation of the threaded piston rod 230 screws the piston rod 230 forward inside the cartridge 225 thus moving the plunger 226 distally.

When the user removes the finger from the injection button 250, the second compression spring 203 moves the driver element 260 in the proximal direction thus also pulling the piston rod guide 240 into its locked position. This proximal movement of the driver element 260 also removes some pressure from the spring 256 such that the toothed interface 261 rides over the teeth 242 of the toothed driver ring 257 whenever a new dose is set by rotation of the driver element 260.

In the third embodiment, the piston rod guide 240 is thus moved axially in and out of engagement with the housing 210 by its connection to the axially movable driver element 260.

In the first position, the dose setting button 245, the driver element 260 and the scale drum 280 rotate together and since the piston rod 230 is kept inrotatable the scale drum 280 climbs helically inside the injection device 201.

In the second position, the driver element 260, the scale drum 280 and the drive assembly 255 all rotate together under influence of the released torsion spring 270 such that the piston rod 230 is moved in the distal direction.

Generally speaking for all embodiments, the scale drum 80, 180, 280 is coupled to rotate together with the driver element 60, 160, 260 and the engagement between the scale drum 80, 180, 280 and the driver element 60, 160, 260 comprises a part 81, 181, 281 on the scale drum 80, 180, 280 extending through an open slit 62, 162, 262 provided in the driver element 60, 160, 260 such that a thread 82, 182, 282 internally on the scale drum 80, 180, 280 engages the piston rod 30, 130, 230 which is held inrotatable during dose setting.

The scale drum 80, 180, 280 and the part 81, 181, 281 connecting the outer surface of the scale drum 80, 180, 280 with the internal thread 82, 182, 282 are together with the internal thread 82, 182, 282 preferably made as an integral element e.g. through injection moulding. However, it could also be an assembly made from individual components which are connected together by welding, gluing or by another method.

Figure 12:
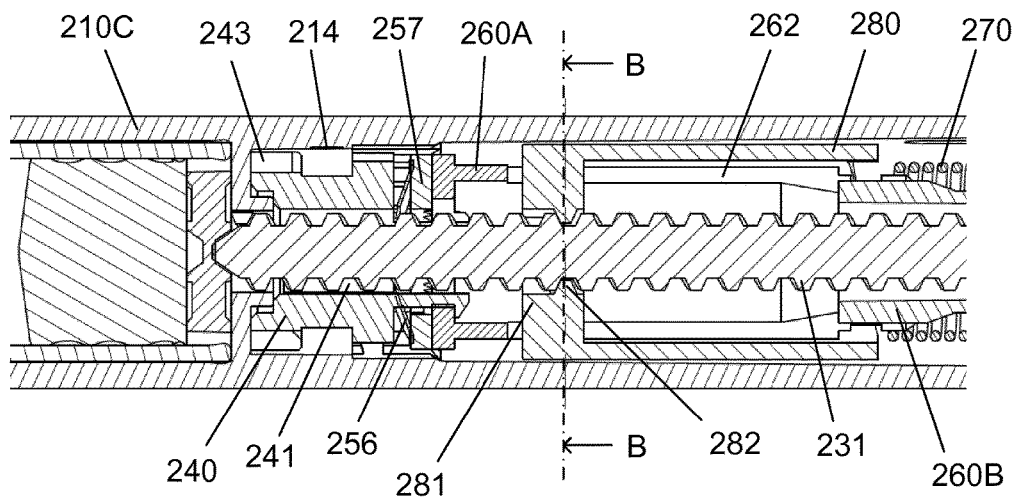
FIG. 12 show an enlarged view of the injection device from FIG. 4 in the first position.
Figure 13:
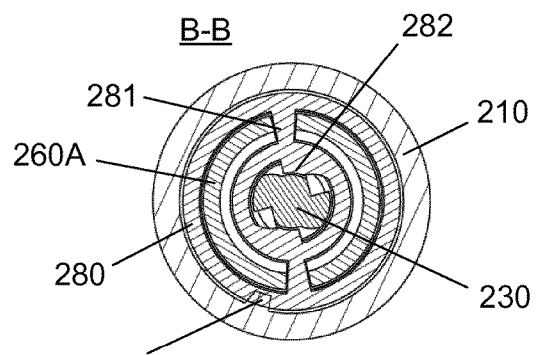
FIG. 13 Show a cross sectional view through the line B-B in FIG. 12.

FIG. 12 discloses the scale drum 280 when it has returned to the zero position after having expelled the set dose. In this position a distal stop flange on the scale drum 280 abut a stop 219 provided internally in the housing 210 as seen in FIG. 13.

FIG. 12 further depicts the abutment between the part 281 of the scale drum 280 and the slit 262 of the driver element 260 (the part 260A). Since this slit 262 has a longitudinal extension, the scale drum 280 is able to move axially while being rotated by the driver element 260. The resulting movement thus being helical due to the threaded engagement with the piston rod 230 being held inrotatable during dose setting. During expelling the driver element 260, the scale drum 280 and the piston rod 230 rotate in unison while the piston rod 230 is being moved axially forward. The movement of the scale drum 280 during dose expelling thus also being helical.

Further in all embodiments, the piston rod 30, 130, 230 is held inrotatable at least in the first position (dose setting mode);

In the first embodiment, the piston rod guide 40 is locked to the housing 10 during dose setting by having the longitudinal tongues 43 locked in tracks 14 inside the housing 10 in the first position thus preventing rotation of the piston rod guide 40 and henceforth the piston rod 30.

In the second embodiment, the piston rod guide 140 is secured to the housing by one or more way ratchet arms 144 which prevent rotation of the piston rod guide 140 in a direction which would course the piston rod 130 to travel in the proximal direction.

In the third embodiment, the piston rod 230 is locked to the housing by having the teeth 243 provided on the piston rod guide 240 to engage tracks 214 provided in the housing 210 in the first position such that the piston rod guide 240 and thus the piston rod 230 is unable to rotate in the first position.

Some preferred embodiments have been shown in the foregoing, but it should be stressed that the invention is not limited to these, but may be embodied in other ways within the subject matter defined in the following claims.

The invention claimed is:

1. A pen-shaped torsion spring driven injection device for apportioning set dose of a liquid drug comprising:
    A housing having a window,
    A piston rod having an external thread,
    A rotatable piston rod guide engaging and driving the piston rod during dose expelling,
    A torsion spring for rotating the piston rod guide,
    A rotatable scale drum having a thread engaging the external thread of the piston rod and carrying a plurality of indicia viewable through the window of the housing,
    A rotatable dose setting member cooperating with the scale drum such that rotation of the dose setting member during dose setting is transformed to a rotation of the scale drum, and wherein
    the piston rod is held inrotatable during dose setting whereby the scale drum rotates helically on the external thread of the piston rod.

2. A pen-shaped torsion spring driven injection device according to claim 1, wherein a driver element is provided and the torsion spring is operable between the driver element and a part of the housing.

3. A pen-shaped torsion spring driven injection device according to claim 2, wherein the driver element is coupled to the dose setting member at least during dose setting.

4. A pen-shaped torsion spring driven injection device according to claim 2, wherein a part of the scale drum extend through the driver element to engage the piston rod.

5. A pen-shaped torsion spring driven injection device according to claim 4, wherein the driver element is provided with a longitudinal opening through which the part of the scale drum extend to engage the piston rod.

6. A pen-shaped torsion spring driven injection device according to claim 2, wherein a force is transmitted from the driver element to the scale drum at least during dose setting.

7. A pen-shaped torsion spring driven injection device according to claim 2, wherein the driver element is axially movable between a first position and a second position by the user activating an injection button (50, 150, 250) coupled to the driver element.

8. A pen-shaped torsion spring driven injection device according to claim 7, wherein the driver element;
    in the first position engages the dose setting member to rotate with the dose setting member and is rotationally decoupled from the piston rod guide, and
    in the second position is rotational decoupled from the dose setting member and engaged with the piston rod guide.

9. A pen-shaped torsion spring driven injection device according to claim 7, wherein the torsion spring is strained to build up torque during rotation of the dose setting member when the driver element in the first position.

10. A pen-shaped torsion spring driven injection device according to claim 7, wherein the torque of the torsion spring is released in response to the drive element being moved axially to the second position.

11. A pen-shaped torsion spring driven injection device according to claim 10, wherein, in the second position, the driver element engages the piston rod guide rotationally such that the piston rod guide and the driver element rotate in unison at least during expelling of the set dose.

12. A pen-shaped torsion spring driven injection device according to claim 1, wherein a mechanism holding the torque of the strained torsion spring is operable between the dose setting member and a part of the housing, such as a spring base.

13. A pen-shaped torsion spring driven injection device according to claim 1, wherein the torsion spring is a helically wounded torsion spring.

14. A pen-shaped torsion spring driven injection device according to claim 1, wherein the torsion spring is a non-helically wounded clock spring.

15. A pen-shaped torsion spring driven injection device according to claim 1, wherein the housing comprises one unitary tubular element surrounding at least the scale drum, the torsion spring and a majority of a cartridge.

* * * * *